United States Patent [19]

Franzone et al.

[11] 4,187,308
[45] Feb. 5, 1980

[54] PHARMACEUTICAL COMPOSITION WITH ANTI-BRONCHOSPASMODIC AND ANTI-TUSSIVE ACTIVITY

[75] Inventors: José S. Franzone; Teresio Tamietto, both of Turin, Italy

[73] Assignee: Istituto Biologico Chemioterapico "ABC" S.p.A., Torino, Italy

[21] Appl. No.: 950,749

[22] Filed: Oct. 12, 1978

[30] Foreign Application Priority Data

Apr. 6, 1978 [IT] Italy ................... 22019 A/78

[51] Int. Cl.$^2$ .............................................. A61K 31/52
[52] U.S. Cl. ..................................................... 424/253
[58] Field of Search ................................. 424/253, 45

[56] References Cited

U.S. PATENT DOCUMENTS 4,085,214  4/1978  Higuchi et al. ................... 424/253

OTHER PUBLICATIONS

DeMartiis et al., Chemical Abstracts 57:16605b (1962).

*Primary Examiner*—Leonard Schenkman
*Attorney, Agent, or Firm*—Bucknam and Archer

[57] ABSTRACT

A pharmaceutical composition with anti-bronchospasmodic and anti-tussive activity which contains an effective amount of the compound of formula

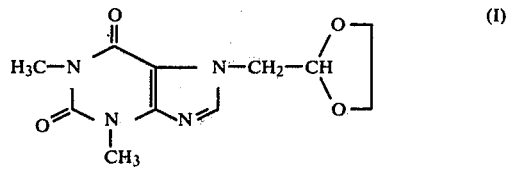

together with at least one pharmaceutically acceptable carrier or diluent. The composition may be administered orally, parenterally, rectally or by means of an aerosol.

7 Claims, No Drawings

PHARMACEUTICAL COMPOSITION WITH ANTI-BRONCHOSPASMODIC AND ANTI-TUSSIVE ACTIVITY

This invention relates to a pharmaceutical composition with anti-bronchospasmodic and anti-tussive activity, characterised by containing as its active principle 2-(7'-theophyllinemethyl)-1,3-dioxolane, of formula (I):

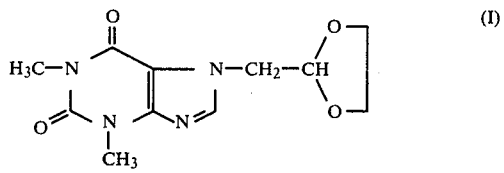

Together with other dioxolanes and dioxanes deriving from theophylline and theobromine, compound (I) was described nearly 20 years ago by U. Avico, F. De Martiis and F. Toffoli (Il Farmaco - Ed.Sc. -vol. XVII- part 2). Reference is made to the determination of the coefficients of distribution between chloroform and water, and between benzene and water.

From the pharmacological aspect, the authors limit themselves to indicating, as a generality for the compounds they considered, that "some of the described products exhibited some hypotensive and coronarodilatory effect of the theophylline type, others some depressive effect", but without giving any numerical data or mentioning the tests used. More specifically, no indication is given of the type of activity, if any, which the authors found for the compound (I).

It has now been surprisingly found that compound (I) exihibits high bronchial and anti-tussive myolytic activity in animals including cats, rabbits and man as well as lower animals, for instance mice, rats, guinea pigs. On the other hand, there is no inurement, it does not modify in vivo the intestinal motility of the rat, it is free from activity on the isolated atria of guinea pigs and does not alter the coronaric flow, and does not induce significant variations in the electrocardiograph trace for the cat and rabbit. When administered intravenously to the cat in doses of 1 to 30 mg/kg, it does not alter the arterial pressure.

It is free from diuretic activity and does not alter choleresis in the rat.

It is absolutely free from side effects on the gastric mucosa.

2-(7'-theophyllinemethyl)-1,3-dioxolane is also characterised by low acute toxicity. The therapeutic index is therefore particularly favourable.

Because of its considerable pharmaco-toxicological properties, 2-(7'-theophyllinemethyl)-1,3-dioxolane constitutes a very useful remedy in human therapy, and particularly for treatment of bronchospasms, bronchial asthma, obstructive chronic bronchitis and spasmodic coughs.

The active principle may be administered orally in the form of tablets or suspensions, parenterally in the form of injectable preparations in phials, through the lungs in the form of an aerosol, or through the rectum in the form of suppositories.

The usual dose is of the order of 0.1–2.5 g per day, according to the patient, the type of affection treated and the method of administration.

The pharmaceutical forms (tablets, suspensions, injectable preparations in phials, suppositories) are normally prepared by the usual pharmaceutical methods.

The example given hereinafter illustrates the preparation of compound (I) by the method of the aforesaid authors.

EXAMPLE

A mixture of 15 g of theophyllineacetic aldehyde, 30 ml of ethylene glycol and 1.5 g of p-toluenesulphonic acid in 600 ml of benzene is heated under reflux in a flask provided with a Marcusson apparatus.

After two hours the separation of the water is complete.

The reaction mixture is washed with 200 ml of a 3.5% aqueous solution of sodium bicarbonate.

The organic phase is dried and concentrated to dryness under reduced pressure, to leave a product residue which is taken up in ethyl ether, separated by filtration and purified by ethanol.

2-(7'-theophyllinemethyl)-1,3-dioxolane is obtained.
M.P. 144°–145°.
Average yield 70%
Analysis: $C_{11}H_{14}N_4O_4$: M.W. 266.26: Calculated: C%, 49.62; H%, 5.30; N%, 21.04. Found: C%, 49.68; H%, 5.29; N%, 21.16.

The toxicological and pharmacological characteristics of the compound (I) are illustrated hereinafter.

DETERMINATION OF ACUTE TOXICITY

The acute oral toxicity was determined both in the mouse and rat, using aminophylline as the reference substance.

The substances were administered in an aqueous 0.5% carboxymethylcellulose suspension at a concentration of 1 ml/10 g of body weight.

After treatment with the respective drugs, the animals were kept under observation for 20 consecutive days, registering their general conditions, behaviour and mortality.

The $DL_{50}$ was calculated by the statistical method of Litchfield and Wilcoxon (1949) J. Pharmacol. Exp. Therap. 96, 99.

Table 1 below gives the $DL_{50}$ results obtained.

TABLE 1

Values of $DL_{50}$ obtained in the mouse and rat for 2-(7'-theophyllinemethyl)-,3-dioxolane and for aminophylline, administered orally.

| Method of administration | 2-(7'-theophyllinemethyl)-1,3-dioxolane $DL_{50}$ | Aminophylline $DL_{50}$ |
|---|---|---|
| | MOUSE | |
| Oral | 862 mg/kg | 535 mg/kg |
| | RAT | |
| Oral | 966 mg/kg | 575 mg/kg |

Under these conditions the acute toxicity of 2-(7'-theophyllinemethyl)-1,3-dioxolane by oral administration was shown to be distinctly less than that of aminophylline, both in the mouse and in the rat. Under the same experimental conditions, 2-(7'-theophyllinemethyl)-1,3-dioxolane was administered intraperitoneally and intravenously, both in the mouse and rat. Results: the $DL_{50}$ in the mouse for i.p. administration was 396 mg/kg, and for i.v. administration was 236 mg/kg.

Likewise, the $DL_{50}$ in the rat for i.p. administration was 426 mg/kg, and for i.v. administration was 315 mg/kg.

Activity of 2-(7'-theophyllinemethyl)-1,3-dioxolane on the smooth bronchial musculature "in vitro" and "in vivo"

"IN VITRO" TESTS (a) Activity on the isolated guinea pig trachea "in toto"

Some thirty albino guinea pigs were used, from which the trachea were withdrawn, after suppression under ether anaesthesia.

The trachea were placed in a bath of 50 ml of a suitably oxygenated Krebs solution, temperature controlled at 37° C. The bottom of the trachea was closed, and the top was connected to a polyethylene tube connected to a transducer connected to a polygraph, for measuring the volume difference by the partly modified method of D. Jamieson (1962), Brit. J. Pharmacol and Chemiotherapy 19, 286.

Both the trachea and polyethylene tube were filled with the Krebs solution. The responses to acetylcholine and to histamine were investigated on the trachea prepared in this manner, both before and after administering the product to the bath. Table 2 below shows the results obtained in this investigation.

TABLE 2

Effect of 2-(7'-theophyllinemethyl)-1,3-dioxolane on the isolated guinea pig trachea "in toto".

| | No. experiments | Product g/ml | Inhibition % | $DE_{50}$ g/ml |
|---|---|---|---|---|
| acetylcholine chloride | 4 | $40.10^{-6}$ | −25% | |
| | 4 | $80.10^{-6}$ | −29% | |
| | 4 | $200.10^{-6}$ | −50% | $1990.10^{-6}$ |
| | 4 | $400.10^{-6}$ | −65% | |
| histamine dihydrochloride | 4 | $40.10^{-6}$ | 0% | |
| | 4 | $200.10^{-6}$ | −54% | |
| | 4 | $400.10^{-6}$ | −78% | $175.10^{-6}$ |
| | 4 | $800.10^{-6}$ | −100% | |

"IN VIVO" TESTS (a) Comparative activity of 2-(7'-theophyllinemethyl)-1,3-dioxolane and theophylline on the bronchospasm in the guinea pig The method used in these tests was that of Konzett and Rosler (1940) Arch. Exp. Path. Pharmak. 191, 71, with certain modifications by Collier H.O.J. (1960), Brit. J. Pharmacol. 15, 290.

Male guinea pigs having a weight of 300-450 grams were used, under anaesthesia by urethane (1 g/kg i.p.).

The animals were suitably prepared by inserting a cannule into the jugular vein for intravenous administration, and the trachea was connected to a pump for artificial respiration (Palmer) adapted for small animals, and which was operated at a frequency of about 70 insufflations per minute. The pneumogram was recorded via a transducer on a polygraph (Battaglia Rangoni).

The bronchospasm was induced in the guinea pig by intravenous injection of acetylcholine or histamine.

After two equal responses to the acetylcholine of histamine, the drugs under study were administered by i.v.

(b) Comparative anti-tussive activity of 2-(7'-theophyllinemethyl)-1,3-dioxolane and aminophylline in the guinea pig.

For these tests we used the method of Charlier and Coll. (1961) Arch. Inter. Pharmacodyn. 134, 306, with slight modifications.

This method consists essentially of exposing the guinea pig to a 3% histamine dihydrochloride aerosol for three minutes, suitably recording the cough of the animal before and after oral treatment with an anti-tussive substance.

The apparatus for inducing and recording the cough consisted of a hermetically sealed perspex box (20×20×15 cm), connected on one side to an aerosol compressor by way of a cannula, and connected at the top to another cannula suitably connected to a transducer of a polygraph.

For these tests, spotted male guinea pigs were used, having a weight of 350-400 grams, and which had been fasting for 12 hours.

Tables 3, 4, 5 hereinafter give the results obtained.

TABLE 3

Inhibiting effect of 2-(7'-theophyllinemethyl)-1,3-dioxolane and theophylline on the bronchospasm induced by acetylcholine chloride in the guinea pig.

| Substance | Dose mg/kg i.v. | No. of animals | % change in endobronchial pressure after i.v. administration of 0.2 mg/kg acetylcholine chloride and graduated doses of drugs Average ± SE | % inhibition with respect to controls | $DE_{50}$ mg/kg |
|---|---|---|---|---|---|
| Controls | — | 12 | 190.6 ± 34.2 | — | — |
| 2-(7'-theophyllinemethyl)-1,3-dioxolane | 0.5 | 6 | 152.5 ± 17.7 | −20.0% | |
| | 1 | 6 | 129.1 ± 28.9 | −32.1% | 1.3 |
| | 2 | 6 | 50.0 ± 11.6 | −73.8% | |
| | 4 | 6 | 26.7 ± 12.5 | −86.0% | |
| Theophylline | 1 | 6 | 125.2 ± 23.5 | −34.4% | |
| Theophylline | 2 | 6 | 104.0 ± 31.5 | −45.3% | 2.3 |
| Theophylline | 4 | 6 | 72.5 ± 19.1 | −62.0% | |

TABLE 4

Inhibiting effect of 2-(7'theophyllinemethyl)-1,3-dioxolane and theophylline on the bronchospasm induced by histamine dihydrochloride in the guinea pig.

| Substance | Dose mg/kg i.v. | No. of animals | % change in endobronchial pressure after i.v. adminisration of 0.05 mg/kg histamine dihydrochloride and graduated doses of drugs Average ± SE | % inhibiton with respect to controls | $DE_{50}$ mg/kg |
|---|---|---|---|---|---|
| Controls | — | 12 | 178.6 ± 38.4 | — | |
| 2-(7'-theophyllimemethyl)-1,3-dioxolane | 0.05 | 6 | 100.0 ± 27.8 | −44.9% | |
| | 0.1 | 6 | 70.0 ± 15.0 | −60.9% | |
| | 1.0 | 6 | 33.3 ± 4.9 | −81.4% | 0.075 |
| | 2.0 | 6 | 8.3 ± 1.9 | −95.4% | |
| Theophylline | 0.5 | 6 | 110.0 ± 27.2 | −38.5% | |
| Theophylline | 1.0 | 6 | 84.0 ± 14.7 | −53.0% | 0.82 |

TABLE 4-continued

Inhibiting effect of 2-(7'theophyllinemethyl)-
1,3-dioxolane and theophylline on the bronchospasm induced
by histamine dihydrochloride in the guinea pig.

| Substance | Dose mg/kg i.v. | No. of animals | % change in endobronchial pressure after i.v. adminisration of 0.05 mg/kg histamine dihydrochloride and graduated doses of drugs Average ± SE | % inhibiton with respect to controls | $DE_{50}$ mg/kg |
|---|---|---|---|---|---|
| line | | | | | |
| Theophylline | 2.0 | 6 | 47.5 ± 6.3 | −73.5% | |

As can be seen from Tables 3 and 4, it is apparent that the antibronchospasmodic effect of 2-(7'-theophyllinemethyl)-1,3-dioxolane is about twice as high as that of theophylline for the spasm induced by acetylcholine, and about eleven times as high as that of theophylline for the spasm induced by histamine.

TABLE 5

Activity of 2-(7'-theophyllinemethyl)-1,3-dioxolane
and aminophylline (administered orally) or the cough
induced in the guinea pig by 0.05 histamine dihydrochloride aerosol.

| Treatment | Dose mg/kg | No. of coughs Before treatment | 3 hours after treatment | % change with respect to before treatment | % change with respect to controls | $DE_{50}$* mg/kg |
|---|---|---|---|---|---|---|
| Controls | — | 180 ± 2.2 | 15.4 ± 0.8 | −14.6% | — | |
| 2-(7'-theophyllinemethyl)-1,3-dioxolane | 0.1 | 16.4 ± 1.2 | 11.0 ± 0.8 | −32.8% | −28.6 | 0.88 |
| | 0.5 | 16.0 ± 0.9 | 7.8 ± 1.2 | −51.2% | −49.3% | |
| | 1.0 | 16.2 ± 1.5 | 3.27 ± 1.1 | −79.8% | −78.8% | |
| | 10.0 | 16.7 ± 2.1 | 3.85 ± 0.8 | −76.9% | −75.0% | |
| Aminophylline | 10 | 19.0 ± 2.3 | 14.0 ± 1.1 | −26.3% | − 9.1% | |
| Aminophylline | 15 | 16.2 ± 1.8 | 11.2 ± 1.4 | −30.9% | −23.3% | 22.5 |
| Aminophylline | 25 | 18.0 ± 2.9 | 6.3 ± 1.2 | −65.0% | −59.1% | |
| Aminophylline | 5:0 | 15.2 ± 2.6 | 4.4 ± 1.1 | −71.1% | −71.4% | |

*The dose $DE_{50}$ has been calculated on the percentages with respect to the controls.

Table 5 shows that the anti-tussive activity of 2-(7'-theophyllinemethyl)-1,3-dioxolane for the histamine aerosol is considerably greater (about 26 times) than that of aminophylline.

The pharmaceutical forms for the composition according to the invention are illustrated by the following examples:

(a) A 0.400 g tablet contains:
| | |
|---|---|
| 2-(7'-theophyllinemethyl)-1,3-dioxolane | 0.200 g |
| mannitol | 0.070 g |
| microcrystalline cellulose | 0.052 g |
| colloidal silica | 0.026 g |
| talc | 0.024 g |
| P.V.P. | 0.020 g |
| magnesium stearate | 0.008 g |

(b) 100 g of suspension contains:

| | |
|---|---|
| 2-(7'-theophyllinemethyl)-1,3-dioxolane | 2.50 g |
| 70% sorbitol | 50.00 g |
| levilite | 4.00 g |
| emulsifiers | 1.20 g |
| soluble orange extract | 1.00 g |
| methyl p-hydroxybenzoate | 0.13 g |
| methyl p-hydroxybenzoate | 0.13 g |
| distilled water, necessary quantity to make up | 100 g |

For pediatric use, the dose is a minimum of 4 g of said suspension two or three times a day.

(c) Each 10 ml vial contains:
| | |
|---|---|
| 2-(7'-theophyllinemethyl)-1,3-dioxolane | 0.100 g |
| bidistilled apyrogenic sterile water, quantity necessary to make up | 10 ml |

(d) Each 2.6 g suppository for adults contains:
| | |
|---|---|
| 2-(7'-theophyllinemethyl)-1,3-dioxolane | 0.300 g |
| fatty acid glycerides | 2.300 g |

(e) Each 1.6 g pediatric suppository contains:
| | |
|---|---|
| 2-(7'-theophyllinemethyl)-1,3-dioxolane | 0.100 g |
| fatty acid glycerides | 1.500 g |

(f) The aerosol composition, which is administered by a mechanical inhalator, contains:

| | |
|---|---|
| 2-(7'-theophyllinemethyl)-1,3-dioxolane | 0.100 g |
| bidistilled apyrogenic sterile water, quantity necessary to make up 10 ml | |

Many carriers and diluents may be used for the preparation of the pharmaceutical compositions of this inventions, provided that they are non-toxic to the living organism. Water, ethyl, alcohol, acqueous ethyl alcohol, propylene glycol may be used. Obviously chloroform, benzene should be avoided.

The preparations contain a minimum of 0.080 g of the compound of formula I per unit dose and preferably 0.1 g. The maximum amount of compound I per unit dose is 3 g but preferably 2.5 g.

What we claim is:

1. A pharmaceutical composition with anti-bronchospasmodic and anti-tussive activity in the form of an aerosol for pulmonary administration containing an effective amount of the compound of formula I

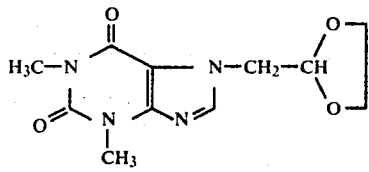

together with at least one pharmaceutically acceptable carrier or diluent.

2. A method of treating a living subject affected by bronchospasms, bronchial asthma, obstructive chronic bronchitis and spasmodic coughs, which comprises administering to said living subject an effective amount of a compound of formula I

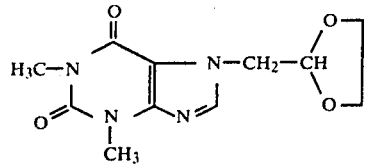

3. The method according to claim 2 wherein a tablet containing said compound is administered orally.

4. The method according to claim 2 wherein a suspension containing a minimum of 4 g of said compound of formula I is administered at least twice a day.

5. The method according to claim 2 wherein suppositories containing said compound are administered rectally.

6. The method according to claim 2 wherein said compound in the form of an aerosol is administered through the lungs of said living subject.

7. The method according to claim 2 wherein said compound is administered in the dose of 0.1–2.5 g per day.

* * * * *